United States Patent
Tanassi et al.

(10) Patent No.: US 9,380,939 B2
(45) Date of Patent: Jul. 5, 2016

(54) FUNDUS PHOTOGRAPHING APPARATUS

(71) Applicant: NIDEK CO., LTD., Gamagori-shi, Aichi (JP)

(72) Inventors: Cesare Tanassi, Susegana (IT); Raffaella Bisson, Padua (IT); Mauro Campigotto, Camposampiero (IT); Simone Pajaro, Padua (IT); Ettore Cerulli, Veggiano (IT)

(73) Assignee: NIDEK CO., LTD., Gamagori-shi (JP)

( * ) Notice: Subject to any disclaimer, the term of this patent is extended or adjusted under 35 U.S.C. 154(b) by 363 days.

(21) Appl. No.: 13/930,748

(22) Filed: Jun. 28, 2013

(65) Prior Publication Data
US 2014/0028976 A1 Jan. 30, 2014

(30) Foreign Application Priority Data
Jul. 27, 2012 (JP) .................................. 2012-167105

(51) Int. Cl.
 A61B 3/00 (2006.01)
 A61B 3/15 (2006.01)
 A61B 3/12 (2006.01)

(52) U.S. Cl.
 CPC .. *A61B 3/152* (2013.01); *A61B 3/12* (2013.01)

(58) Field of Classification Search
 CPC .............. A61B 3/12; A61B 3/14; A61B 3/15; A61B 3/152; A61B 3/113
 USPC .......................................... 351/200–221, 246
 See application file for complete search history.

(56) References Cited

U.S. PATENT DOCUMENTS

| | | | |
|---|---|---|---|
| 7,572,009 B2 | 8/2009 | Suzuki | |
| 2003/0157464 A1 | 8/2003 | Tanassi et al. | |
| 2007/0132951 A1* | 6/2007 | Suzuki | ........................... 351/206 |
| 2009/0287276 A1* | 11/2009 | Greenberg et al. | ............. 607/54 |

FOREIGN PATENT DOCUMENTS

| | | |
|---|---|---|
| EP | 1 609 405 A1 | 12/2005 |
| EP | 2 057 938 A1 | 5/2009 |
| EP | 2 147 634 A1 | 1/2010 |
| EP | 2 394 569 A1 | 12/2011 |
| EP | 2 395 343 A1 | 12/2011 |
| JP | A-2003-235800 | 8/2003 |

* cited by examiner

OTHER PUBLICATIONS

Oct. 29, 2013 Extended European Search Report issued in European Application No. 13176135.5.

*Primary Examiner* — Ricky Mack
*Assistant Examiner* — Gary O'Neill
(74) *Attorney, Agent, or Firm* — Oliff PLC

(57) ABSTRACT

A fundus photographing apparatus includes: a photographing unit including a fundus illumination optical system to illuminate a fundus of a patient's eye and a fundus photographing optical system having a light receiving element to obtain a fundus image of the illuminated eye; and an alignment unit to position the photographing unit with the eye based on a predetermined alignment reference position. The alignment unit includes: an extracting part to extract, by image processing, an image region formed by reflection light from a portion other than the fundus from the fundus image obtained by the fundus photographing optical system; a gravity center calculating part to determine, by arithmetic processing, a gravity center position of the extracted image region; and a control part to perform alignment control of the photographing unit with the eye based on the calculated gravity center position and the alignment reference position.

7 Claims, 11 Drawing Sheets

FUNDUS PHOTOGRAPHING APPARATUS

CROSS-REFERENCE TO RELATED APPLICATIONS

This application is based upon and claims the benefit of priority from the prior Japanese Patent Application No. 2012-167105, filed Jul. 27, 2012, the entire contents of which are incorporated herein by reference.

BACKGROUND OF THE INVENTION

1. Field of the Invention

The present invention relates to a fundus photographing apparatus for photographing a fundus of an eye of a patient or examinee.

2. Related Art

There is known a fundus photographing apparatus for observing or photographing a fundus in focus (e.g., see Patent Document 1). A fundus photographing apparatus in Patent Document 1 is configured to observe and photograph a fundus of a patient's eye and also function as a perimeter for testing a visual function of the eye by projecting a test target on each measurement point on a fundus (retina) based on a response of the patient.

RELATED ART DOCUMENTS

Patent Documents

Patent Document 1: JP 2003-235800 A

SUMMARY OF INVENTION

Problems to be Solved by the Invention

Meanwhile, the above type of fundus photographing apparatus needs to properly maintain an alignment state between the eye and a photographing unit in order to restrain the generation of flare (components of illumination light reflected by a portion of a patient's eye other than a fundus) due to movement or rotation of the eye caused during test or observation.

The present invention has a purpose to provide a fundus photographing apparatus capable of appropriately observing and photographing a fundus of a patient's eye.

Means of Solving the Problems

To achieve the above purpose, one aspect of the invention provides a fundus photographing apparatus comprising: a photographing unit including a fundus illumination optical system to illuminate a fundus of a patient's eye and a fundus photographing optical system having a light receiving element to obtain an image of the fundus of the patient's eye illuminated by the illumination optical system; and an alignment unit arranged to position the photographing unit with the patient's eye based on a predetermined alignment reference position, the alignment unit including: an extracting part to extract, by image processing, an image region formed by reflection light from a portion other than the fundus from the fundus image obtained by the fundus photographing optical system; and a gravity center calculating part to determine, by arithmetic processing, a gravity center position of the image region extracted by the extracting part; and a control part to perform alignment control of the photographing unit with respect to the patient's eye based on the gravity center position calculated by the gravity center calculating part and the alignment reference position.

Effects of the Invention

The present invention can provides a fundus photographing apparatus capable of appropriately observing and photographing a fundus of a patient's eye.

DESCRIPTION OF EMBODIMENTS

Figure 1:
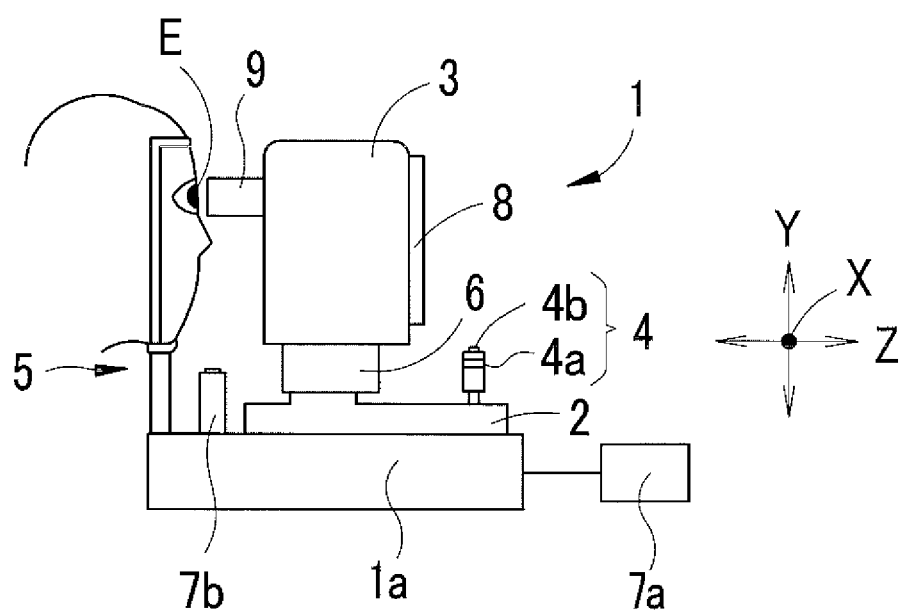
FIG. 1 is an external configuration view of a fundus photographing apparatus.
Figure 2:
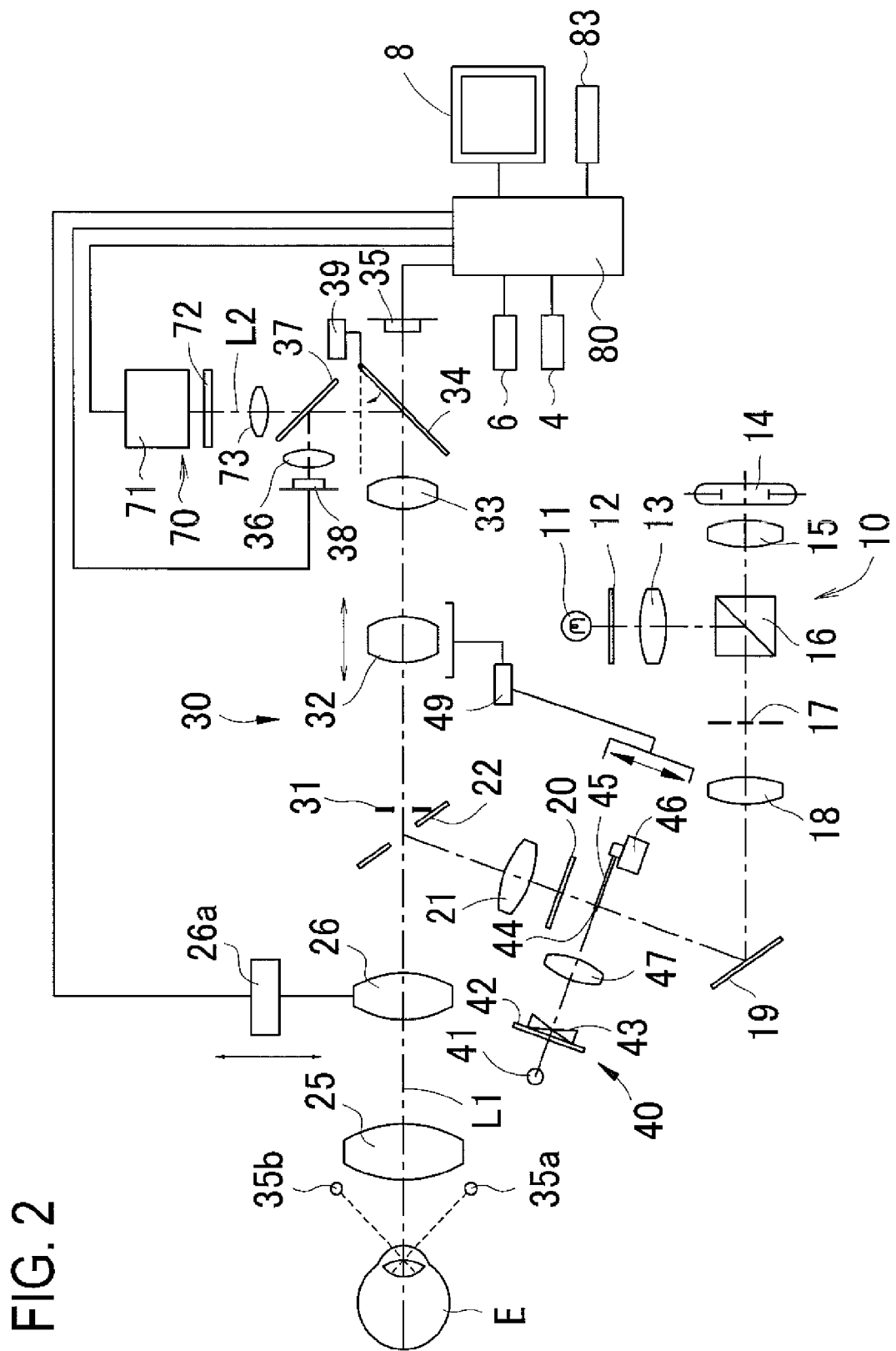
FIG. 2 is a diagram to explain optical systems and a control system of the fundus photographing apparatus in a first embodiment.

A detailed description of a preferred embodiment of the present invention will now be given referring to the accompanying drawings. As an example of a fundus photographing apparatus, the following explanation is made on a fundus photographing apparatus capable of serving for both the fundus observation and photographing and the fundus visual field test. FIG. 1 is an external configuration view of the fundus photographing apparatus. FIG. 2 is a diagram to explain optical systems and a control system of the fundus photographing apparatus in a first embodiment.

In FIG. 1, a fundus photographing apparatus 1 includes a base 1a, a movable table 2 configured to be movable relative to the base 1a in a right and left direction (X direction) and a back and forth (working distance) direction (Z direction), a photographing unit (a main unit) 3 provided to be movable in the right and left direction (X direction), an up and down direction (Y direction), and the back and forth direction (Z direction) relative to an eye E of a patient or examinee by a drive part 6 provided on the movable table 2, and a head supporting unit 5 fixed to the base 1a to support the face (head) of the patient. The photographing unit 3 contains optical systems and a control system mentioned later.

On an examiner side of the photographing unit 3, there are provided a joystick 4, a controller 7a, and a monitor 8. The joystick 4 is used to relatively move the photographing unit 3 with respect to the eye E. When the joystick 4 is tilted, the movable table 2 is slid on the base 1a in the X and Z directions by a sliding mechanism. The joystick 4 is provided with a rotation knob 4a on the periphery and a switch 4b on the top. By rotation of the rotation knob 4a, the drive part 6 is driven to move the photographing unit 3 in the Y direction. In response to an input signal from the switch 4b, an operation of photographing a fundus image and so on is executed. The controller 7a is an input means to set various photographing and testing conditions and others and provided as a mouse, a keyboard, a touch panel (attached to the monitor 8), etc. The monitor 8 displays various test results as well as observed and photographed images of the eye E. For instance, a fundus observation screen, an anterior segment observation screen, a visual field test screen, a rehabilitation screen, and others are displayed on the monitor 8. On a patient side of the photographing unit 3, there are provided a photographing window 9 through which a patient peers the inside of the apparatus, and a response button 7b with which a patient enters a response signal during a visual function test of an eye (retina) and others.

In FIG. 2, the optical systems include an illumination optical system 10 (a fundus illumination optical system) to illuminate a fundus of a patient's eye, an observation and photographing optical system 30 (a fundus photographing optical system) to observe and photograph a fundus, an anterior segment, and others of a patient's eye, a focus mark projecting optical system 40 to project a focus mark on a fundus, an alignment mark projecting optical system to project alignment mark light onto an anterior segment, and a target presenting optical system 70 to guide the visual line of the patient (the eye E).

<Illumination Optical System>

The illumination optical system 10 has a photographing illumination optical system and an observing illumination optical system. In the present embodiment, the photographing illumination optical system includes a photographing light source (a visible light source) 14 to irradiate a visible light beam, a condenser lens 15, a ring slit 17 having a ring-shaped aperture, a relay lens 18, a mirror 19, a black point plate 20 having a black point at a center thereof, a relay lens 21, a perforated mirror 22, and an objective lens 25.

In the present embodiment, furthermore, the observing illumination optical system includes an illumination light source 11 to irradiate a near infrared light beam, an infrared filter 12 that transmits near infrared light, a condenser lens 13, a dichroic mirror 16 placed between the condenser lens 13 and the ring slit 17, an optical system including the ring slit 17 to a perforated mirror 22, and an objective lens 25.

<Observing and Photographing Optical System>

The observing and photographing optical system 30 includes a fundus observing optical system, a fundus photographing optical system, and an anterior segment observing optical system. This fundus observing optical system includes the objective lens 25, a photographing diaphragm 31 located near an aperture of the perforated mirror 22, a focusing lens 32 movable in a photographing optical axis direction, an image forming lens 33, and a flip-up mirror 34. On an optical path in a reflecting direction of the flip-up mirror 34, there are arranged a dichroic mirror 37 having the property of transmitting visible light, a relay lens 36, and a two-dimensional imaging element 38 for observation, which is sensitive to light in an infrared region, to photograph a fundus image illuminated by an infrared light source. The flip-up mirror 34 is inserted in an optical path during fundus observation and is retracted from the optical path during fundus photographing by an inserting/removing mechanism 39. Although the present embodiment uses a two-dimensional imaging element 38 as a light receiving element to be used in alignment with the eye E, the light receiving element is not limited thereto. For example, in the present embodiment, different light receiving elements are used as the two-dimensional imaging element 38 for observing a moving image formed by the infrared light source and a two-dimensional imaging element 35 for observing a still image formed by the light source 14, but a single light receiving element (an image pickup device) may perform both the moving image observation and the still image photographing. Furthermore, it may be arranged such that an avalanche photodiode is used as the light receiving element, the illumination optical system 10 includes a laser source to scan a fundus of the eye E, and the observing and photographing optical system 30 receives a laser beam reflected from the fundus and generates a fundus image (a moving image and a still image).

The fundus photographing optical system shares the objective lens 25 and the optical system from the photographing diaphragm 31 to the image forming lens 33 with the fundus observing optical system. The fundus photographing optical system further includes the two-dimensional imaging element 35 for photographing, which is sensitive to a visible range, to create a fundus image of the fundus illuminated by the light source 14. The photographing diaphragm 31 is disposed in a substantially conjugated position with respect to a pupil of the eye E through the objective lens 25. The focusing lens 32 is moved in an optical axis direction by a moving mechanism 49 provided with a motor.

With the above configuration, during fundus observation, the light emitted from the light source 11 is converged on near the pupil of the eye E by the objective lens 25 and then is diffused to illuminate the fundus. Reflection light from the fundus passes through the objective lens 25, the aperture of perforated mirror 22, photographing diaphragm 31, focusing lens 32, image forming lens 33, flip-up mirror 34, dichroic mirror 37, and relay lens 36 and forms an image on the two-dimensional imaging element 38. During fundus photographing, the reflection light from the fundus illuminated by the light source 14 passes through the objective lens 25, the aperture of perforated mirror 22, photographing diaphragm 31, focusing lens 32, and image forming lens 33 and forms an image on the two-dimensional imaging element 35.

The anterior segment observing optical system includes infrared light sources 35a and 35b which emit infrared light, the objective lens 25, and an anterior segment observation auxiliary lens 26 (hereinafter, referred to as an auxiliary lens) and shares the optical system from the perforated mirror 22 to the two-dimensional imaging element 38 with the fundus observing optical system. The infrared light sources 35a and 35b are a pair of rectangular LEDs arranged symmetrically with respect to a photographing optical axis (optical axis) L1 and project finite marks (rectangular marks extending in a vertical direction relative to a patient's eye) formed by divergent light at a predetermined projection angle to a cornea of the eye E. Accordingly, these marks represent an alignment state of the photographing unit 3 with the eye E in a three dimensional direction and also illuminate the entire anterior segment.

The auxiliary lens 26 is inserted or removed from the optical path by actuation of a drive means 26a. When the auxiliary lens 26 is put on the optical axis L1, the anterior segment and the two-dimensional imaging element 38 are placed in a substantially conjugate relationship. Specifically, during observation of the anterior segment, the auxiliary lens 26 is placed on the optical axis L1 and the anterior segment picked up by the two-dimensional imaging element 38 is displayed on the monitor 8. On the other hand, during fundus observation, the auxiliary lens 26 is retracted from the optical path by actuation of the drive means 26*a*, so that the two-dimensional imaging element 38 is placed in a substantially conjugate relationship with the fundus and the picked-up fundus image is displayed on the monitor 8.

<Focus Mark Projecting Optical System>

The focus mark projecting optical system 40 includes an infrared light source 41, a slit mark plate 42, two deflection prisms 43 attached to the slit mark plate 42, a lever 45 obliquely placed on an optical path of the illumination optical system 10, a spot mirror 44 attached to the lever 45 and placed in a conjugate position with the fundus, a rotary solenoid 46, and a projection lens 47. The lever 45 is placed on the optical axis. The spot mirror 44 is attached to the tip of the lever 45 so as to be placed in a position outside the optical axis. Accordingly, during fundus observation, the reflection light from the spot mirror 44 is projected onto the position on the fundus outside the optical axis L1.

Light of the slit mark plate 42 is split by the deflection prism 43 and then reflected by the spot mirror 44 via the projection lens 47, and is projected on the fundus via the relay lens 21, perforated mirror 22, and objective lens 25. While the fundus is not in focus, a mark image (focus marks S1 and S2) of the slit mark plate 42 is not conjugated with the fundus and thus is projected in separated positions on the fundus (see FIG. 4A). In this case, based on a detection result of the separated state of the focus marks S1 and S2, the moving mechanism 49 drives the focusing lens 32 and the focus mark projecting optical system 40 to be moved in sync with each other in the optical axis direction. On the other hand, when the fundus falls into focus, the focus marks S1 and S2 are conjugated with the fundus and thus coincident with each other (see FIG. 4B). When fundus photographing is to be performed while the fundus is in focus, the lever 45 is retracted from the optical path by rotation of a shaft of the rotary solenoid 46.

<Target Presenting Optical System>

The target presenting optical system 70 shares the objective lens 25 to the flip-up mirror 34 of the observing and photographing optical system 30 and further includes a two-dimensional scanning projector (a target presenting device) 71, a screen 72, and a lens 73. The projector 71 includes, even though not illustrated, a plurality of light sources to irradiate laser beams in predetermined colors (e.g., red, green, and blue), a collimator lens to collimate each laser beam, a dichroic mirror whereby the laser beams each collimated by the collimator lens are made coaxial with each other, a lens to be moved on the optical axis to change an irradiation diameter of the coaxial laser beam, and a scan part to make the light passing through the lens scan on the screen 72. Turn-on/off of each light source and actuation of the scan part are controlled by a control part 80 mentioned later.

Since the target presenting optical system 70 uses a light source, the size, shape, and others of the target(s) to be projected on a fundus can be changed. By combinations of laser beams to be irradiated from the light sources, not only monochrome target(s) but also color target(s) can be presented. For instance, a color anomaly (dyschormatopsia) test chart, ISHIHARA, and visual function test targets using colors of specific wavelength lights (e.g., red, blue, and green) can be presented. This makes it possible to specify the presence/absence of color anomaly, abnormal cone (color anomaly to specific color(s)), or the like. Further, various types of visual function tests can be conducted by use of a single test device.

In the present embodiment, an image (target or targets) projected on the screen 72 placed in a substantially conjugated position with the fundus is formed on the fundus through some intermediate optical systems. As an alternative, however, a laser beam irradiated from the projector 71 may be projected directly on the fundus to form various targets.

<Control System>

The control part 80 is connected to the above optical systems and control system to control various operations. The control part 80 is also connected to a memory 83 serving as a storage part. This memory 83 stores in advance various programs and information such as a configuration setting file. The control part 80, the illumination optical system 10, and the observing and photographing optical system 30 constitute an alignment means. The control part 80 executes, serving as the alignment means, the alignment control based on a detection result of a flare region included in a photographed image. Thus, the control part 80 stores in advance luminance threshold information to extract pixels constituting the flare region.

For instance, the control part 80 detects alignment marks from an anterior segment image picked up by the two-dimensional imaging element 38. The control part 80 further causes the monitor 8 to display the fundus image picked up by the two-dimensional imaging element 35 and also performs focusing of the fundus based on the separated state of the focus marks. In the present embodiment, furthermore, when the fundus visual field test is to be performed, the flare region is extracted from the fundus image picked up by the two-dimensional imaging element 38 and alignment is performed to move the photographing unit 3 in a direction to remove the flare. This reduces the influence of the generation of flare due to eye movement or rotation occurring during the visual field test. Thus, the alignment of the eye E and the photographing unit 3 can be maintained properly.

Operations of the fundus photographing apparatus including the above configuration will be explained below. The following explanation is made on the operations of performing the eye visual field test and then photographing the fundus. When a visual field test mode is set by operation of the controller 7*a*, a visual field test screen is displayed on the monitor 8. The control part 80 drives the drive means 26*a* to position the auxiliary lens 26 on the optical axis L2 and turns on the infrared light sources 35*a* and 35*b*. In this state, a patient peers through the photographing windows 9. Then, the anterior segment is illuminated and the rectangular alignment marks are projected on a cornea.

On the other hand, the control part 80 drives and controls the projector 71 to form a fixation target on the screen 72. Specifically, the control part 80 adjusts the output of a laser beam according to a scanning angle of the scan part to form a high-luminance fixation target on a low-luminance background. To be concrete, the output (luminance) of the laser beam of each light source is raised at a fixation target presenting position corresponding to the optical axis L1 and is decreased at other positions in the background. Accordingly, the bright target (high luminance) is formed on a dark background (low luminance) of the screen 72. The image (the fixation target) formed on the screen 72 is projected on the fundus of the patient's eye located in a substantially conjugated position with the screen 72 via the lens 73, flip-up mirror 34, image forming lens 33 to objective lens 25.

Figure 3:
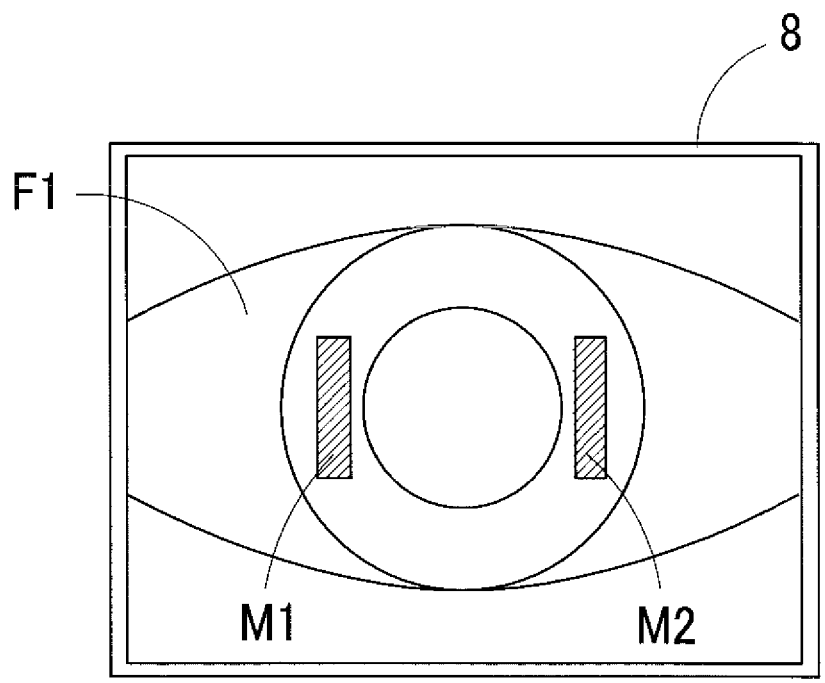
FIG. 3 is a diagram showing an anterior segment image displayed on a monitor.

While the eye E is guided by the fixation target, positioning (alignment) using the anterior segment image is performed. An example of an anterior segment image displayed on the monitor 8 is shown in FIG. 3. When rectangular alignment marks M1 and M2 appear on an anterior segment image F1, the control part 80 performs positioning (alignment) of the photographing unit 3 with the eye E based on light receiving results.

Specifically, the control part 80 moves the photographing unit 3 in up, down, right, and left (XY) directions so that an intermediate point determined from the alignment marks M1 and M2 comes to coincide with the pupil center determined from the anterior segment image. Further, the control part 80 moves the photographing unit 3 in the back and forth (Z) direction relative to the eye E to make positioning in the working distance direction so that the interval between the alignment marks M1 and M2 is a predetermined distance. For the details of the alignment operations, refer to WO 2008/062527.

When the control part 80 determines that the alignment in a three dimensional direction falls in an alignment permissible range, the control part 80 turns off the infrared light sources 35a and 35b and retracts the auxiliary lens 26 from the optical path, and turns on the light source 11. The display of the monitor 8 is changed to the fundus image picked up by the two-dimensional imaging element 38. The focusing of the fundus is performed by use of the focus mark projecting optical system 40.

Figure 4A:
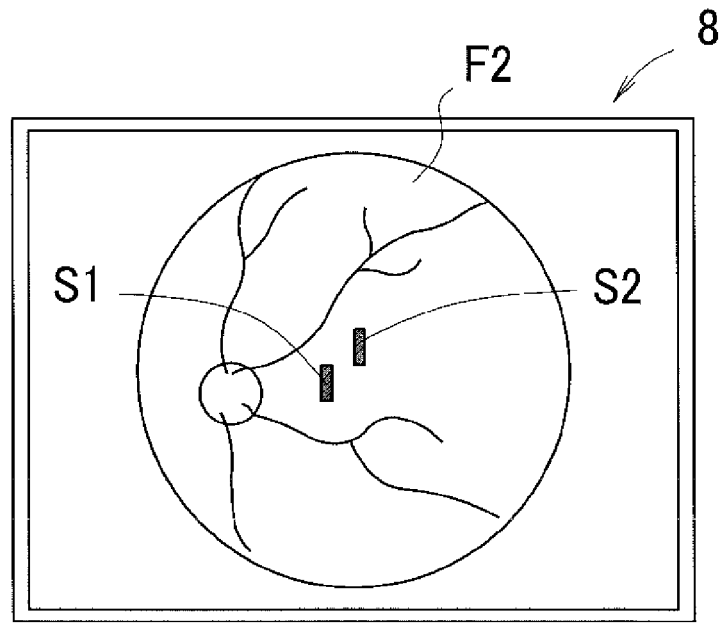
FIGS. 4A and 4B are diagrams showing fundus images displayed on the monitor.
Figure 4B:
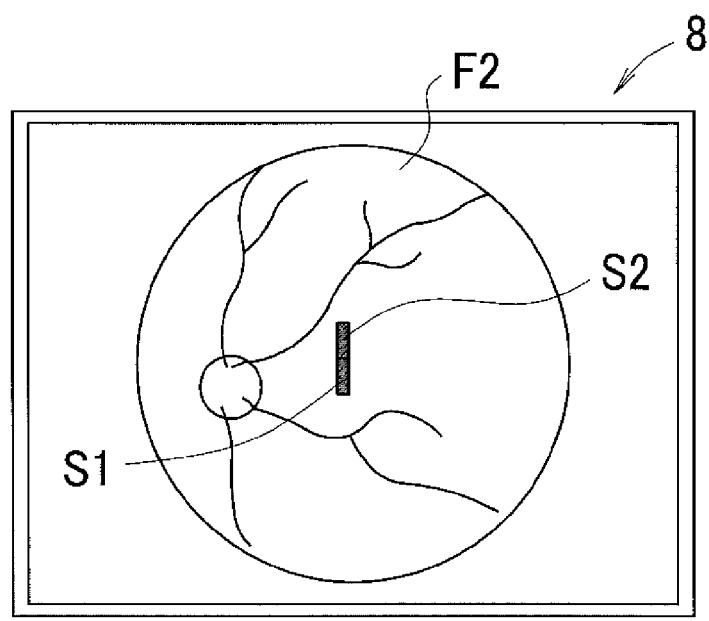

FIGS. 4A and 4B show examples of a fundus image F2 displayed on the monitor 8; specifically, FIG. 4A illustrates the fundus image F2 obtained when the fundus is out of focus and FIG. 4B illustrates the fundus image F2 obtained when the fundus is in focus. The control part 80 specifies the positions of the focus marks S1 and S2 based on the luminance distribution in a photographing range of the two-dimensional imaging element 38. The distance (a separated state) between the detected focus marks S1 and S2 is determined and, based on this detection result, the focusing is conducted. In the case of an out-of-focus condition as shown in FIG. 4A, the control part 80 moves the focusing lens 32 on the optical axis L1 so that the focus marks S1 and S2 coincide. When the control part 80 judges that the focus condition is proper, the focus adjustment is completed.

When the fundus image F2 comes to clearly appear on the monitor 8, the control part 80 starts alignment to correct positional displacement between the eye E and the photographing unit 3 (the optical axis L1) caused by movement and rotation of the eye E during the visual field test and tracking to correct the positional displacement of the presented targets. In the visual field test, the test targets are repeatedly presented on different sites of the fundus to examine the visual function. This takes a fixed time. Thus, the presenting position of the test targets is apt to be displaced under the influence of micromotion of the eye and others. Then, when the tracking of the fundus is performed by the control part 80, the influence of the eye micromotions and others is canceled out and the test targets are projected on desired positions of the fundus. However, there is a case where a fundus image includes flare due to rotation of the eye E in the test. If a characteristic portion is less likely to be clearly detected under the influence of flare, it is difficult to correct the presenting position of the test targets by tracking. On the other hand, when the anterior segment observation and the fundus observation are switched over by insertion/removal of the auxiliary lens 26, alignment detection using the anterior segment image is not allowed while the fundus image is being observed. In the present embodiment, therefore, the alignment is performed in such a manner that the flare region is extracted by image processing of the fundus image and the photographing unit 3 is moved in a direction in which the fundus image does not include flare. Accordingly, the tracking operation based on detection of a characteristic portion is appropriately performed.

Figure 5:
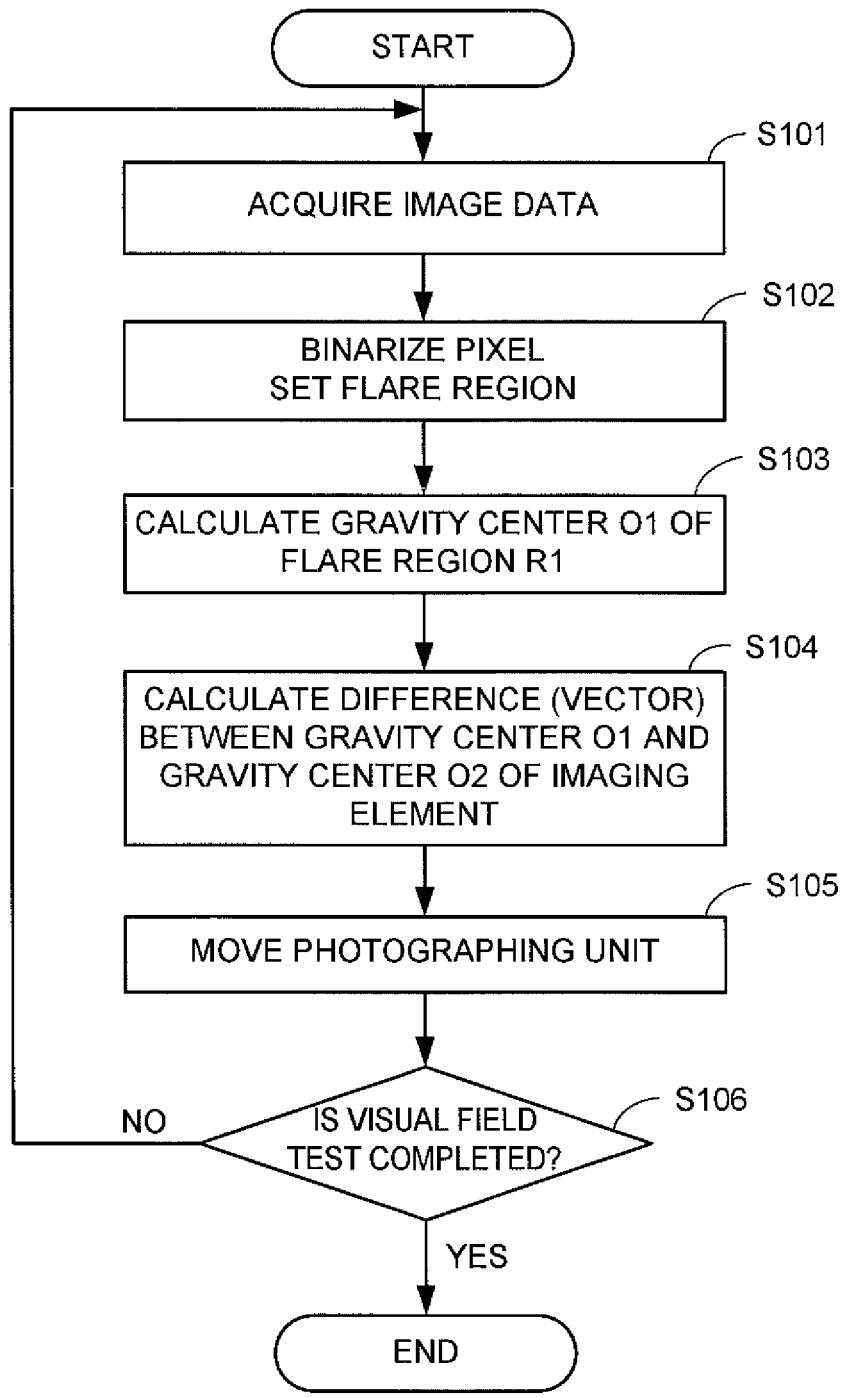
FIG. 5 is a flowchart of the principle of alignment operation using a flare region.
Figure 6A:
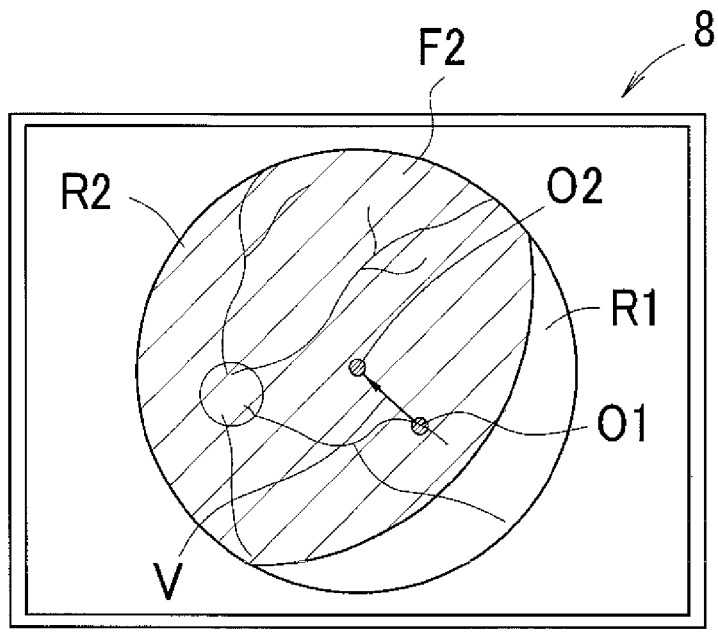
FIGS. 6A and 6B are diagrams to explain alignment.
Figure 6B:
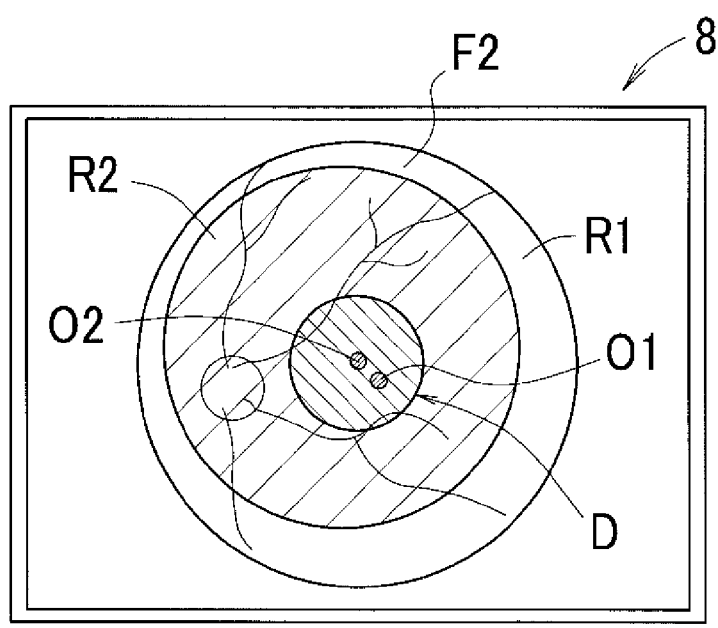

FIG. 5 is a flowchart showing the principle of alignment operations using the flare region according to the present invention. FIGS. 6A and 6B are diagrams to explain the alignment.

After completion of focusing, at step S101, the control part 80 acquires a fundus image (image data) from the two-dimensional imaging element 38 at predetermined steps (time intervals). At that time, if the illumination light projected on the fundus of the eye E is reflected by a different portion from the fundus due to movement or rotation of the eye E and hence enters the two-dimensional imaging element 38, in the fundus image, reflection light (flare) reflected from the other portion than the fundus is superimposed on the fundus image. For instance, when the illumination light reflected by the cornea enters the two-dimensional imaging element 38, whity flare occurs on the periphery of the fundus image. As the flare included in the photographed image, there are known not only flare generated by illumination light reflected by a cornea of a patient's eye during fundus photographing but also flare generated by illumination light reflected inside a crystal lens of a patient's eye.

At step S102, successively, the control part 80 serves as a flare region extracting means to binarize each pixel constituting the obtained fundus image (image data) based on threshold information of luminance stored in advance in the memory 83. Accordingly, a group of pixels having higher luminance than the threshold is extracted as a flare region R1 and a group of pixels having lower luminance than the threshold is sectioned as the other region (non-flare region) R2. Herein, as shown in FIG. 6A, the flare appears on the right side of the fundus image on the drawing sheet. By binarization, the flare region R1 is set (extracted) on the right side of the fundus image on the drawing sheet. The threshold is set in advance as a threshold whereby the flare region R1 and the other image regions are separated. To be concrete, the luminance threshold is determined in advance in a manner that luminance values at which flare is extracted are determined by experiments or the like.

At step S103, the control part 80 serves as gravity center calculating means to determine the gravity center (position) O1 (x, y) of an image moment of the extracted flare region R1 by image processing. The gravity center O1 (x, y) indicated herein is a gravity center based on the information of luminance of an image and is calculated by well-known image processing moment calculation. For example, it is calculated by the following expression (1).

(Expression 1)

$$O1(x, y) = \sum_x \sum_y xy \cdot f(x, y) \quad (1)$$

In this expression (1), f (x, y) is a luminance value of a pixel corresponding to the coordinate (x, y). Specifically, in the expression (1), the gravity center position in the x direction and the gravity center position in the y direction are separately determined to set the gravity center O1 (x, y) of the flare region R1.

At step S104, the control part 80 determines a difference between the coordinate of the gravity center O1 of the flare region R1 determined at step S103 and a predetermined alignment reference position, and thereby determines a moving direction (vector) of the photographing unit 3. In the present embodiment, the predetermined alignment reference position is assumed as the coordinate of the gravity center O2 (the position at which an imaging plane of the two-dimensional imaging element 38 and the optical axis L1 intersect each other) of the two-dimensional imaging element 38. At step S105, the control part 80 drives the drive part 6 to move the photographing unit 3 so that the gravity center O1 of the flare region R1 and the gravity center O2 (the optical axis L1) of the two-dimensional imaging element 38 come to close to each other. It is noted that the gravity center O1 of the flare region R1 and the gravity center O2 of the two-dimensional imaging element 38 do not always have to coincide with each other as long as a moving amount of the photographing unit 3 is determined so that the flare region is not contained in the fundus image.

The control part 80 may change the moving speed of the photographing unit 3 according to the difference (vector) between the gravity center O1 and the gravity center O2. In other words, as the difference is larger and the vector V is longer, the moving speed of the photographing unit 3 is increased. On the other hand, as the difference is smaller and the vector V is shorter, the control part 80 decreases the moving speed of the photographing unit 3. By this control, the positional displacement between the eye E and the photographing unit 3 is easily reduced according to the extent of movement or rotation of the eye E. The present embodiment exemplifies the gravity center of the imaging element as an example of the alignment reference position, but does not limit the invention thereto. It is only necessary to set the alignment reference position by a predetermined position on a light receiving element set to adjust the photographing unit and a patient's eye in a predetermined positional relationship.

Subsequently, at step S106, it is determined whether or not the visual field test is completed. When it is determined at step S106 that the visual field test is not completed, the control part 80 returns the program to step S101 and repeatedly acquires image data through the two-dimensional imaging element 38. On the other hand, the visual field test is determined to be completed at step S106, the alignment process is terminated.

Meanwhile, in case fundus photographing mentioned later is carried out in the course of the eye E blinking, such a flare as surrounding the entire periphery of a fundus image as shown in FIG. 6B may be generated. This flare does not directly result from movement and rotation of the eye E. Thus, if such a photographed image is obtained at step S101, there is a possibility that alignment between the eye E and the two-dimensional imaging element 38 is not correctly controlled.

It is therefore preferable that the detection result of the flare generated in other than movement or rotation of the eye E is not reflected in the above alignment processing. The gravity center O1 of the flare region R1 set based on the flare generated around the periphery of the fundus image is near the center (the gravity center O2) of the fundus which is assumed as the alignment reference point. In the case where the gravity center O1 is present in a predetermined range centered on the alignment reference point (the gravity center O2), the alignment processing based on the flare region R1 is disabled. Specifically, the predetermined range centered on the alignment reference point is defined as an inactive region D. If the coordinate of the gravity center O1 of the flare region R1 determined at step S104 falls within the inactive region D, the control part 80 does not perform the alignment processing and returns to step S101 to execute a processing to acquire another image data. Specifically, when the coordinate of the gravity center O1 of the flare region R1 is in the predetermined range from the alignment reference point, the alignment control based on the coordinate of the gravity center O1 of the detected flare region R1 is not performed. The presence of this inactive region D can reduce unnecessary alignment processing. The range (a coordinate region) of the inactive region D is set by determining the gravity center of flare generated during eye blinking by experiments or the like in advance.

Figure 7:
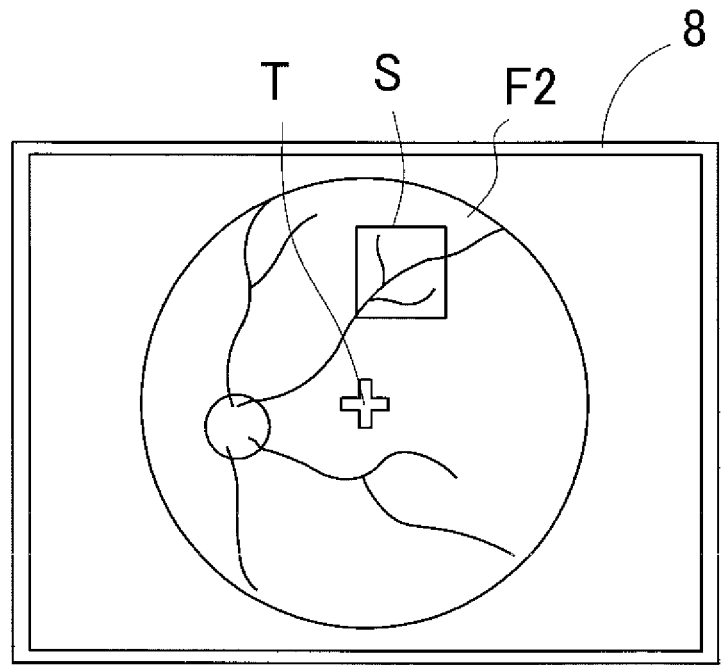
FIG. 7 is a diagram to explain the principle of tracking operation.

Next, an explanation is made on the principle of tracking operation to correct the position of test targets to be presented by the target presenting optical system 70 following movement or rotation of an eyeball. FIG. 7 is a diagram to explain the principle of tracking operation, in which the fundus image F2 and a presenting position of a target T are displayed. While checking the fundus image F2 displayed on the monitor 8, an examiner first operates the controller 7a to specify a characteristic point (a region) such as a papillary area and a blood vessel on the fundus image F2. The characteristic point may be automatically extracted by image processing. Based on an input signal from the controller 7a, the control part 80 stores the coordinate of the characteristic point and the predetermined range centered on the characteristic point as a reference area S in the memory 83, and displays a frame indicating the reference area S on the monitor 8. The control part 80 obtains, by image processing in the reference area, the information such as the shape of the characteristic portion and luminance distribution (characteristics information to determine a characteristic portion by image processing) and stores them in the memory 83.

When the control part 80 detects the moving amount of the characteristic point (the reference area S) on the monitor 8, the presenting position of the target (test target) to be projected on the fundus is corrected so as to coincide with the selected point on the monitor 8 to follow the motion (movement) of the eye E. This reduces the influence of rotation or the like of the eye E caused during a test and allows the test target to be projected correctly on a desired position on the fundus, thereby accurately performing the visual function test.

While the above alignment and tracking are being performed, the control part 80 presents a predetermined test target at each measurement points on the fundus in accordance with a visual field test program stored in advance in the memory 83. The control part 80 drives and controls the projector 71 to randomly change the presenting position of the test target and adjusts the output of the light source of the projector 71 to change luminance of the target. On the other hand, a patient continues to hold fixation and, if recognizes the test target, pushes the response button 7b. Based on an input signal, the control part 80 stores, in the memory 83, the luminance of the test target as response information on the sensitivity of the patient to the target recognizable at a relevant measurement point. In the absence of a response from the patient, the control part 80 stores, in the memory 83, the luminance of the test target as response information on the sensitivity of the patient to the target unrecognizable at a relevant measurement point.

Figure 8:
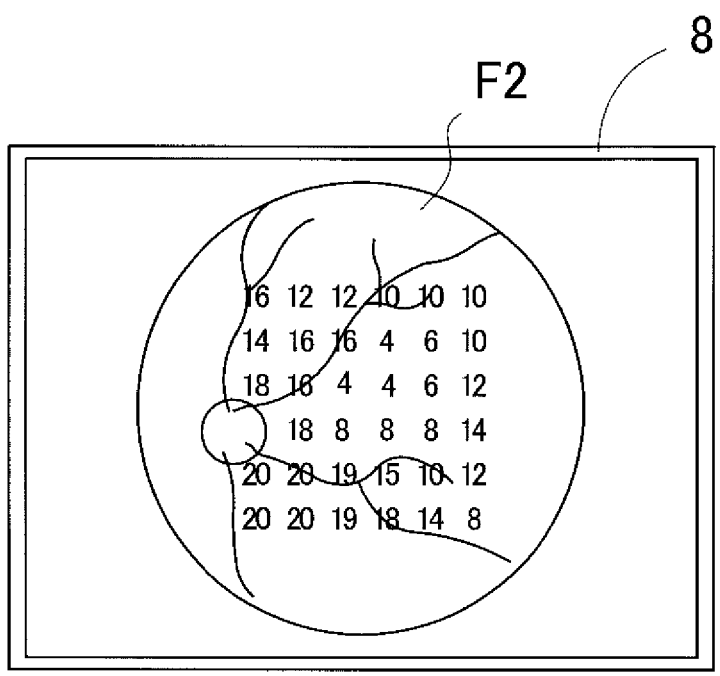
FIG. 8 is a diagram showing an example of distribution of visual function sensitivity.

Upon completion of sensitivity measurement at all the measurement points, as illustrated in FIG. 8 showing an example of a distribution diagram of the visual function sensitivity, the control part 80 displays the result of the visual function test of the eye on the monitor 8. To be concrete, the control part 80 causes the monitor 8 to display a schematic diagram representing a distribution state of sensitivity at all the measurement points. In FIG. 8, attenuation values of luminance of the presented targets are used to display sensitivity distribution, in which the sensitivity distribution is expressed in a difference from the highest luminance. That is, it is determined that as the value displayed on the monitor 8 is higher, the sensitivity in that portion is higher.

After completion of the visual field test, the control part 80 turns off the light source 11 that irradiates near infrared light and turns on the visible light source 14. The inserting/removing mechanism 39 is driven to retract the flip-up mirror 34 from the optical path. The reflection light from the fundus illuminated by the visible light passes through the fundus photographing optical system and then falls on the two-dimensional imaging element 35.

As a result of the visual field test, if a disease is found in a portion near a macula having high sensitivity, a patient is likely to have difficulty seeing things. In such a case, therefore, it is possible to perform rehabilitation based on the visual field test results to allow a patient to see things by using another fundus portion still having a visual function as an alternate portion (PRL: Preferred Retinal Locus) of the macula, instead of using the diseased macula.

While a rehabilitation screen is displayed on the monitor 8, the positioning between the eye E and the photographing unit 3 is conducted in the same steps as above and the reference area S is set in the characteristic portion of the fundus image. The examiner operates the controller 7a to set the PRL on the fundus image displayed on the monitor 8. The control part 80 stores, in the memory 83, the coordinate of the designated PRL (the coordinate on the monitor) and the information to associate the coordinate with the reference area S, and causes the monitor 8 to display a mark (not shown) indicating the selected PRL to the examiner. The PRL is preferably determined in consideration of safety of fixation of a patient' eye, reading speed on characters and others, other visual function test results, the presence/absence of (the possibility of generation of) diseases detected by visual observation of a color fundus image, and others.

After completion of the above settings, the examiner guides the patient to move his/her visual line so as to bring the mark close to the fixation target T displayed at the center of the monitor 8. As the direction of the visual line is changed, the macula located in the projected position of the fixation target T is gradually moved. At that time, the control part 80 continuously tracks the reference area S set as the characteristic point and thus determines the moving amount of the visual line from an initial position by use of the moving amount of the reference area S determined by image processing. Based on the detection result (the moving amount), the displayed position of the mark on the monitor 8 is sequentially changed, so that the approaching state of the PRL and the fixation target T is visually checked. On the other hand, the control part 80 detects the approaching state of the position of the fixation target T and the position of the set mark from the moving amount of the reference area S.

When the mark is detected to have approached within a predetermined range, the control part 80 issues an informing sound at regular intervals from a speaker not shown or the like. A reference distance from the fixation target T to generate the informing sound is stored in advance in the memory 83. As the distance between the mark and the fixation target T is shorter, the state of the informing sound is changed. This can make it easy for the patient to know the approaching degree.

Figure 9A:
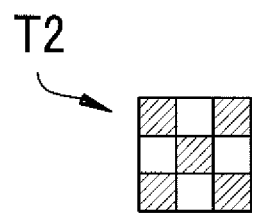
FIGS. 9A to 9C show examples of stimulation marks to be used in rehabilitation.

When the mark almost coincides with the fixation target T, the control part 80 continuously generates the informing sound for a predetermined time and drives and controls the projector 71 to change the shape of the fixation target T. Herein, the fixation target T presented in a cross shape is changed to a mark T2 of a checkered flag pattern having white and black areas alternately arranged as shown in FIG. 9A. This change of the state of the fixation target T allows the patient to visually recognize the coincident state of the PRL (mark) and the fixation target T. If the white and black areas of the mark T2 are alternately blinked (flicker stimulation), the coincident state of the PRL and the fixation target can be more clearly presented. When blinking target gives stimulation to the retina of a patient, it is expected to enhance the retinal sensitivity. When the above rehabilitation is repeated, the patient gradually masters a new way of viewing using PRL.

The above explanation is given to the example of using flicker stimulation as the mark T2. As alternatives, an examiner may select the mark T2 from among various static marks (simple-shaped marks, non-blinking marks) and dynamic marks (e.g., flicker stimulation). Furthermore, the shape and the area of the mark T2, blinking frequency of dynamic marks, and other conditions can be arbitrarily determined. In the case of using a projector as the target presenting device 71 as in the present embodiment, the outputs of laser beams of multiple colors are adjusted to arbitrarily form the mark T2 in various shapes, colors, and sizes (for example, a mark consisting of a plurality of bars extending in a horizontal direction and alternately blinking). A stimulation target can be formed by combining such various conditions; color, shape, and size. Accordingly, a more effective stimulation mark suitable for a patient's disease can be selected.

Figure 9B:
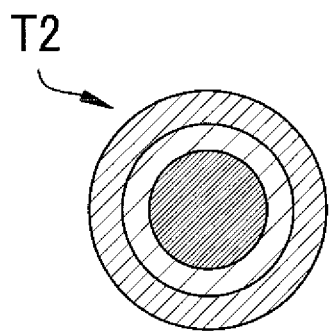
Figure 9C:
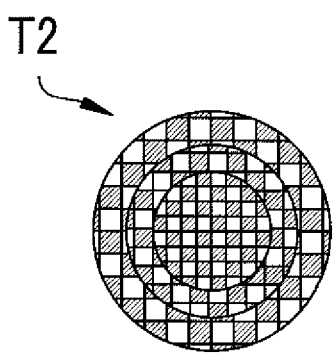

For instance, as a result of a visual field test performed using color targets, the color combination of the flicker stimulation shown in FIG. 9A may be set in different colors selected from the colors of wavelengths to which a retina is highly sensitive. It is thus expected that PRL is stimulated more appropriately, resulting in suitable improvement of the visual function of an eye. Furthermore, as shown in FIG. 9B, the shape of a stimulation target is designed as concentric circles having an inner circle near the center and an outer circle near the outer circumference, and at least two colors in each circle are repeatedly blinked. In this case, the blinking frequency of the inner circle and the blinking frequency of the outer circle may be set to be different (the frequency of the inner circle is higher) so that the inner circle stimulates the retina more strongly. As shown in FIG. 9C, a concentric circular target may be formed by combining variously-shaped targets. Herein, an example is illustrated in which a concentric circular mark is combined with checker flag patterns. When such a stimulation mark having a complicated shape is blinked, it is expected that PRL of the retina is more stimulated. Other than the geometric target, an examiner may prepare various targets in advance according to patient's preferences and store them in the memory 83.

When a test target is to be created by an examiner, a registration screen for test targets is displayed on the monitor 8 (not illustrated). The registration screen includes various commands prepared to determine the shape, color, blinking condition, and others of the targets. The examiner depicts a test target in a desired shape on the monitor 8 by operating the controller 7a and also associates various conditions such as color and blinking state. After completion of setting the test targets as explained above, a newly created test target is stored in the memory 83 in response to an input signal from the controller 7a. In the above manner, rehabilitation suitable for each patient's disease is more effectively performed. If the retinal function of a patient is recovering by rehabilitation, the shape and condition of a mark to be used are changed so that suitable treatment for a patient's disease state is performed.

Various pieces of information (e.g., information on a reference area S, a relative coordinate of the mark T2, and others) of rehabilitation using PRL mentioned above are all stored in a configuration setting file of the memory 83 in association with ID information of a patient. Accordingly, when the patient undergoes a re-test (a feedback test) at a later date, various information and the patient information are both retrieved from the configuration setting file, so that rehabilitation can be repeated under the same conditions as in the previous time. This enables checking on a change in a condition of the patient from previous rehabilitation and allows a treatment under the same conditions as needed. Furthermore, another treatment using new rehabilitation can be performed depending on the result of the re-test.

The above embodiment shows the example of performing rehabilitation using the fundus photographing apparatus, but the present invention is not limited thereto. As an alternative is to install a configuration setting file of the memory 83 in which various rehabilitation conditions (patient's name, coordinate information of fixation targets, coordinate of a PRL range for rehabilitation with respect to a coordinate position of a fixation target, blinking pattern of mark T2, blinking frequency of mark T2, etc.) in a household personal computer PC of a patient. In this case, the patient is allowed to easily carry out rehabilitation at regular intervals at home without needing to go to a hospital or clinic. Herein, an example that a patient carries out rehabilitation at home will be explained below. The following explanation is based on the premise that a patient has an appropriate communication environment such as a personal computer and LAN at home.

Conventionally, to more clearly see an object, a person with low visual acuity would enlarge the object by use of a lens such as eyeglasses or display the object in an enlarged size on a PC. In a case where the object is text, there is known a method in which the text is converted to information such as sound other than information needing a visual function, thereby allowing a person to recognize the object. However, those methods could not give a chance to improve the visual acuity (visual function) of a patient having a low visual acuity. On the other hand, it is expected to improve the remaining visual function of a low-vision patient by rehabilitation training using the above PRL.

To improve the visual function (visibility) of a low-vision patient needing rehabilitation, repeating the training using PRL is required. However, such a low-vision patient needs to be assisted by a third person to go to a hospital or clinic. This hospital visit is a burden on both the patient and the third person. On the other hand, since general-purpose computers PC are widely used in the world, it can be said that the environment to perform rehabilitation at home is available to low-vision persons. Therefore, the present invention provides a special software (a program) allowing low-vision persons to carry out rehabilitation by using their household personal computers PC. This software enables easy at-home visual function training using the PRL.

A software SW contains a configuration setting file SWA in which conditions of a feedback test (rehabilitation) of a patient are stored, the file SWA being stored in the memory 83 of the main unit of the fundus photographing apparatus 1, and an external storage file SWB in which information of the configuration setting file SWA transferred from the fundus photographing apparatus 1 is stored. It is to be noted that the software SW, the configuration setting file SWA, and the external storage file SWB are not illustrated in any figures.

In the configuration setting file SWA, there are stored various conditions for rehabilitation performed by the fundus photographing apparatus, such as the patient's name, the coordinate of fixation targets, the coordinate of PRL to the fixation targets, the shape and blinking frequency of the stimulation targets. Furthermore, this file SWA also stores information such as a rehabilitation period set by an examiner, an interval at which each section of rehabilitation is performed, and the number of times the rehabilitation is carried out. Those pieces of information are automatically transferred to the configuration setting file SWA every time when the control part 80 of the fundus photographing apparatus 1 performs the rehabilitation of each patient or transmitted based on a manual operation of an examiner. The external storage file SWB is stored in a well-known device in which the file SWB downloadable from website or installable. The device is selectable from devices available in general-purpose computers, such as CD, DVD, and Dongle.

Figure 10:
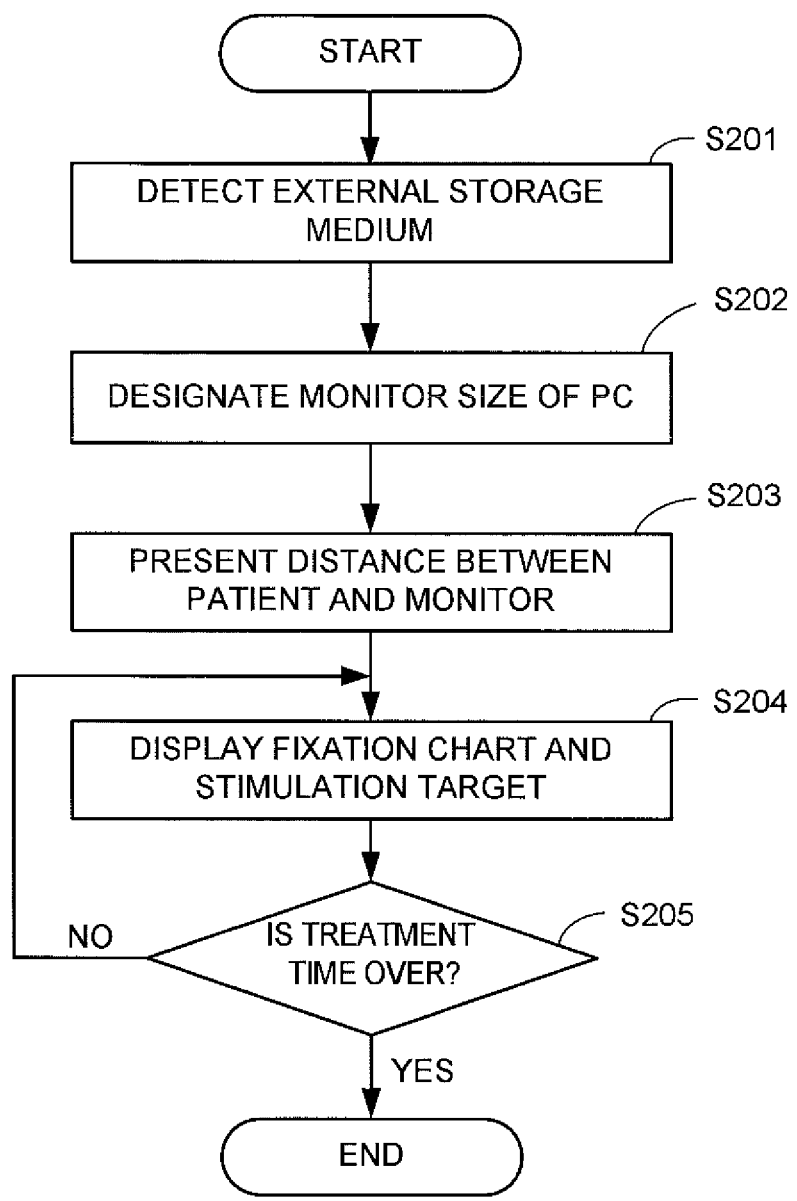
FIG. 10 is a flowchart of a procedure of executing at-home rehabilitation.
Figure 11:
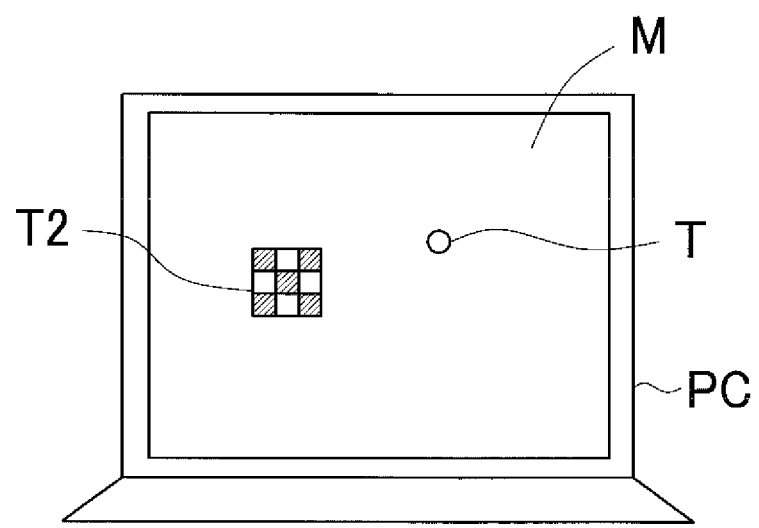
FIG. 11 shows an example of a display screen of a monitor of a household personal computer of a patient.

Next, the procedure of executing a rehabilitation program at home will be explained below. FIG. 10 is a flowchart of the procedure of executing the rehabilitation program at home. FIG. 11 shows an example of a display screen of a monitor M of a household personal computer PC of a patient.

A patient first visits a hospital or clinic (an examiner) and undergoes the rehabilitation using the fundus photographing apparatus 1 and then various conditions such as PRL and the coordinate of stimulation targets are determined. The control part 80 stores the set various conditions in the configuration setting file SWA. Furthermore, in response to operation of the controller 7a, the control part 80 transfers the information from the configuration setting file SWA to a storage medium in which the external storage file SWB has been stored (Patient's unique rehabilitation condition: Eye Fitness Software), and stores the information in the file SWB.

At step S201, while the household personal computer PC of the patient is running, when the control part (not shown) of the personal computer PC detects that the external storage file SWB is installed therein by download from a website of a clinic having an authentication function or by insertion of a storage medium such as a CD, a DVD, or the like in the computer PC, at step S202, the control part causes the monitor M to display a screen to guide input of a screen size of the monitor M. Accordingly, the positional relationship between the fixation target and the PRL on the monitor M are properly set. When the information on the size of the monitor M is input by the input means (a mouse, keyboard, etc.) operated by the patient (or a care personnel in some cases), the control part of the personal computer PC starts reading the configuration setting file SWA stored in the external storage file SWB and thus starts to execute a software (Eye Fitness Software) to perform at-home rehabilitation.

At step S203, the control part causes the monitor M to display a message indicating the distance between the patient and the monitor M. Based on this, the patient adjusts the distance from himself/herself to the monitor M. The message may be informed in the form of another means such as a sound to a low-vision patient. At step S204, the control part causes the monitor M of the personal computer PC to display a fixation target and a flicker stimulation target. At that time, the coordinates of display locations of the fixation target and the flicker stimulation target are set according to the screen size input at step S202. Based on this calculation result, the control part displays the fixation target and the flicker stimulation target on the monitor M. In addition, a treatment time is informed to the patient by the screen display on the monitor M, a sound, or other means. The flicker stimulation target displayed on the monitor M is blinked at the frequency stored in advance in the software SW. While the patient holds fixation on the fixation target, the blinking flicker stimulation target stimulates a predetermined position of the PRL on the retina. Herein, both the fixation target and the stimulation target are displayed on the personal computer PC. As alternative is to generate a sound or the like to instruct the patient to hold fixation on the center of the monitor M without presenting a fixation target, and present only the stimulation target.

At step S205, the control part determines whether or not the treatment time previously set for the patient has elapsed.

When it is determined that the treatment is terminated, the control part informs the patient of the termination of the treatment time by display of the monitor M or a sound, and stores an execution status of the treatment by the patient in the configuration setting file SWA stored in the external storage file SWB. On the other hand, when it is determined that the previously set treatment time does not elapsed, the program is returned to step S204 in which retinal stimulation by flicker stimulation is continued.

After going through the series of rehabilitation steps set by the examiner as above, the patient visits the hospital or clinic (the examiner) again. The at-home rehabilitation program is configured for example to set a training to be repeated for about 10 minutes once every week for three or more months. On the other hand, the information stored in the external storage file SWB at step S204 is input again in the main unit of the fundus photographing apparatus 1 or a personal computer of the examiner via a network of a website (having an authentication function) or a well-known storage medium such as a CD, a DVD, or the like. Accordingly, the control part of the fundus photographing apparatus 1 or the control part of the examiner's personal computer reads the execution status of rehabilitation of the patient stored in the external storage file SWB and thus causes the monitor 8 or the like to display the execution status. Thus, the examiner can easily check whether the patient executed the series of rehabilitation training based on schedule.

In the clinic or hospital, the examiner then performs the visual function test again on the patient by use of the fundus photographing apparatus 1 or other devices. The visual function test may also be conducted by stability of fixation, reading speed on characters and others as well as retinal sensitivity measurement in the above visual field test. The examiner evaluates the at-home rehabilitation result of the patient and also updates the contents of the rehabilitation program based on the evaluation result. At that time, the shape, size, color, and other conditions of the stimulation targets are arbitrarily changed by the examiner according to the improvement extent of the retinal function of the patient. Accordingly, the at-home treatment (rehabilitation) can be more appropriately carried out according to the visibility of the patient.

Studies show that when a visual function deteriorates due to retinal diseases such as age-related retinitis pigmentosa and macular degeneration, rod photoreceptor cells (hereinafter, referred to as "photoreceptor cells") contributing dark adaptation of a retina more drastically decrease in sensitivity than cone contributing light adaptation of a retina. In the embodiment according to the present invention, therefore, a test for dark adaptation of a patient is enabled by use of the above fundus photographing apparatus to early detect a deteriorated retinal function. Accordingly, the above rehabilitation is started from an initial stage of a deterioration in retinal function. It is thus expected to appropriately restrain a further deterioration in retinal function of a patient.

Figure 12:
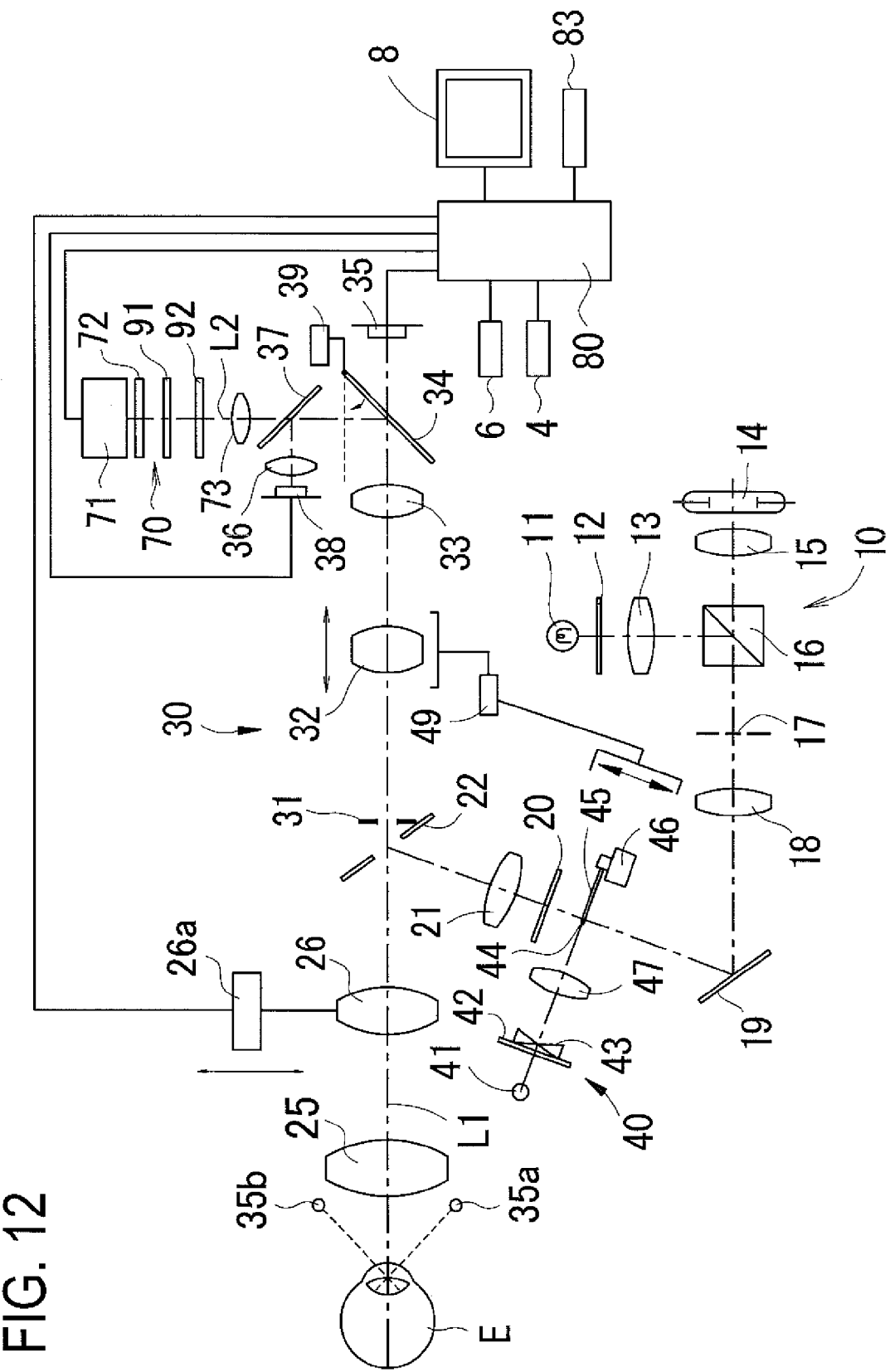
FIG. 12 is a diagram to explain optical systems and a control system of a fundus photographing apparatus in a second embodiment.

Herein, a fundus photographing apparatus in a second embodiment will be explained below. FIG. 12 is a diagram to explain optical systems and a control system of the fundus photographing apparatus of the second embodiment. In the following explanation, similar or identical parts to those in the above fundus photographing apparatus 1 are assigned the same reference signs and their details are not explained. In the present embodiment, a neutral density filter (a light-attenuating filter) 91 for attenuating luminance of the target presenting device 71 and a short pass filter 92 for limiting a light beam of a target output from the target presenting device 71 to a predetermined wavelength (color) are insertably and removeably provided between the target presenting device 71 (the screen 72) and the lens 73. The light beam from the target presenting device 71 is attenuated by the neutral density filter 91 and the background luminance during the visual field test is set in black. On the other hand, the short pass filter 92 is a filter having the property of reducing light having a wavelength band for example exceeding 500 nm and transmitting light having a wavelength band of 500 nm or less. The light beam of a target outputted from the target presenting device 71 is attenuated by the neutral density filter 91 and then restricted to a blue component by the short pass filter 92. In other words, the light (the light beam of the target) attenuated by the neutral density filter 91 is changed to blue by the short pass filter 92. It is to be noted that the positions of the neutral density filter 91 and the short pass filter 92 may be reversed.

Each of the filters 91 and 92 is attached with a lever (not shown). The main unit is provided, near the attachment position of the target presenting device 71, with an opening (not shown) to allow the lever to be inserted or retracted. In this way, the examiner is allowed to insert or retract each of the filters (91, 92) onto the optical axis L2 through the opening of the main unit without opening an outer cover of the main unit. A sensor for detecting the insertion/retraction of each filter (91, 92) may be provided in the main unit. Alternatively, each filter (91, 92) may be connected to a drive mechanism to be automatically inserted or retracted.

With the above configuration, when each filter (91, 92) is inserted in the optical axis L2, the light beam from the target presenting device 71 is limited to a predetermined wavelength band and the visual field test of dark adaptation is enabled. On the other hand, when each filter (91, 92) is retracted from the optical axis L2, the visual field test of light adaptation is enabled. As above, several types of visual field tests can be performed by a single device, so that the examiner is allowed to evaluate the retinal visual function of the patient from various viewpoints.

An example of a visual field test based on dark adaptation of an eye by use of the fundus photographing apparatus configured as above will be explained below. An examiner first places a drop of an ophthalmic solution such as tropicamide in the patient's eye to dilate a pupil of the eye and then leads the patient to a room with less disturbance light such as a dark room, in which the patient's eye is sufficiently dark-adapted in the dark room (e.g., dark adaptation for 30 minutes). On the other hand, the examiner inserts each filter (91, 92) in the opening of the main unit to place them on the optical axis L2. When detecting the attachment of each filter (91, 92), the control part 80 automatically switches to stimulation conditions for the dark-field measurement. It is preferable that the outer appearance of the main unit of the fundus photographing apparatus provided with the visual field test function in the dark adaptation has a color as close to black as possible.

After measurement setup is ready, the patient is made to sit in front of the fundus photographing apparatus 1 and, as in the above visual field test based on the light field, positioning of the patient's eye and the photographing unit 3 is performed. At that time, tracking between the eye and the photographing unit 3 is performed by the same control as above, thereby restraining the influence of fixation disparity caused by the movement of the visual line of the eye or the rotation of the eye. Thus, the test target is properly projected on a desired position on the fundus. In the same routine as above, the test targets are changed and presented. A visual field sensitivity map is created based on responses of the patient.

When the visual field test of the dark adaptation is performed as above, it is expected that an initial stage of the retinal disease can be early detected. The above rehabilitation is started at an early stage before the retinal function disease of the patient advances and the visual function is lost, it is possible to recover the retinal function and restrain the progression of the disease.

Since both the visual field tests of light adaptation and dark adaptation can be performed by a single apparatus, the examiner is allowed to select the visual field tests according to a disease state of the patient. Accordingly, the examiner can efficiently make diagnosis of a patient's eye even if the examiner does not possess a plurality of apparatuses.

Furthermore, it is preferable to measure a visual evoked potential of a patient in various visual field tests and others mentioned above. The visual evoked potential is a potential generated in a visual cortex of a brain when visual stimulation is imparted to a patient's eye. By measuring both of various visual field tests and the visual evoked potential, the measurement results are expected to allow the patient's diseases and others to be comprehensively judged and also to be useful in the rehabilitation condition setting whereby a good response is obtained.

REFERENCE SINGS LIST

1 Fundus photographing apparatus
7a Control part
8 Monitor
10 Illumination optical system
30 Observing and photographing optical system
35, 38 Two-dimensional imaging element
40 Focus mark projecting optical system
70 Target presenting optical system
80 Control part
91 Neutral density filter
92 Short pass filter

The invention claimed is:

1. A fundus photographing apparatus comprising:
a photographing unit including a fundus illumination optical system configured to illuminate a fundus of a patient's eye and a fundus photographing optical system having a light receiving element configured to obtain an image of the fundus of the patient's eye illuminated by the illumination optical system; and
an alignment unit configured to position the photographing unit with the patient's eye based on a predetermined alignment reference position,
the alignment unit including:
an extracting part configured to extract, by image processing, an image region formed by reflection light from a portion other than the fundus from the fundus image obtained by the fundus photographing optical system;
a gravity center calculating part configured to determine, by arithmetic processing, a gravity center position of the image region extracted by the extracting part; and
a control part configured to perform alignment control of the photographing unit with respect to the patient's eye based on the gravity center position calculated by the gravity center calculating part and the alignment reference position.

2. The fundus photographing apparatus according to claim 1, wherein the gravity center calculating part determines a gravity center position of the image region by image processing moment calculation.

3. The fundus photographing apparatus according to claim 1,
wherein the control part does not perform alignment control based on the gravity center position when the gravity center position determined by the gravity center calculating part is within a predetermined range from the alignment reference position.

4. The fundus photographing apparatus according to claim 1, the alignment unit further including a storage part in which a threshold of luminance is stored to binarize pixels constituting the fundus image based on a luminance value, the extracting part configured to extract a pixel of a higher luminance value than the luminance threshold as a pixel forming the image region based on the luminance threshold and the luminance value of each pixel constituting the fundus image.

5. The fundus photographing apparatus according to claim 1, further comprising a target presenting optical system configured to project a fixation target used to guide a visual line of the patient's eye and a test target used for a visual function test of a retina onto the fundus.

6. The fundus photographing apparatus according to claim 1, wherein the image region formed by the reflection light reflected on other than the fundus is flare.

7. The fundus photographing apparatus according to claim 6, wherein the flare is extracted from the fundus image by image processing, and alignment is performed to move the photographing unit in a direction to remove the flare.

* * * * *